US012508443B2

(12) United States Patent
Lin

(10) Patent No.: US 12,508,443 B2
(45) Date of Patent: Dec. 30, 2025

(54) DOSE CONTROL SYSTEM

(71) Applicant: Heron Neutron Medical Corp., Zhubei (TW)

(72) Inventor: Tzung-Yi Lin, Zhubei (TW)

(73) Assignee: HERON NEUTRON MEDICAL CORP., Zhubei (TW)

( * ) Notice: Subject to any disclaimer, the term of this patent is extended or adjusted under 35 U.S.C. 154(b) by 413 days.

(21) Appl. No.: 18/164,367

(22) Filed: Feb. 3, 2023

(65) Prior Publication Data

US 2024/0066319 A1 Feb. 29, 2024

(30) Foreign Application Priority Data

Aug. 11, 2022 (TW) ................................ 111130177

(51) Int. Cl.
*A61N 5/10* (2006.01)

(52) U.S. Cl.
CPC ......... *A61N 5/1031* (2013.01); *A61N 5/1064* (2013.01); *A61N 5/1077* (2013.01)

(58) Field of Classification Search
None
See application file for complete search history.

(56) References Cited

U.S. PATENT DOCUMENTS

2018/0326225 A1 11/2018 Liu et al.
2023/0211186 A1* 7/2023 Liu ..................... A61N 5/1067 250/390.03

FOREIGN PATENT DOCUMENTS

| | | | |
|---|---|---|---|
| CN | 106975162 | A | 7/2017 |
| CN | 106980136 | A | 7/2017 |
| CN | 109011221 | A | 12/2018 |
| JP | 2016-214760 | A | 12/2016 |
| JP | 2018/529437 | A | 10/2018 |
| TW | 201834715 | A | 10/2018 |
| TW | 202112414 | A | 4/2021 |
| WO | 2018/168713 | A1 | 9/2018 |
| WO | WO 2020/111085 | A1 | 6/2020 |
| WO | WO 2020/241415 | A1 | 12/2020 |
| WO | WO 2022/002223 | A1 | 1/2022 |
| WO | WO 2022/002224 | A1 | 1/2022 |
| WO | WO 2022/002230 | A1 | 1/2022 |
| WO | WO 2022/111243 | A1 | 6/2022 |

OTHER PUBLICATIONS

Japanese Office Action for Japanese Application No. 2023-098934, dated Jul. 30, 2024, with English translation.
Extended European Search Report for European Application No. 23159618.0, dated Jan. 4, 2024.
Taiwanese Office Action and Search Report for Taiwanese Application No. 111130177, dated Aug. 30, 2023.

* cited by examiner

*Primary Examiner* — Hoon K Song
(74) *Attorney, Agent, or Firm* — Birch, Stewart, Kolasch & Birch, LLP

(57) ABSTRACT

A dose control system, including a processing device configured to obtain the real drug concentration in plasma of a patient. The processing device is further configured to calculate the corrected dose rate distribution datum based on the real drug concentration in plasma and a set of correction coefficients. The processing device is further configured to calculate the irradiation time based on the corrected dose rate distribution datum and the prescribed dose distribution datum. The processing device is further configured to control the irradiation device to irradiate the patient for the irradiation time.

8 Claims, 3 Drawing Sheets

100

300

DOSE CONTROL SYSTEM

CROSS REFERENCE TO RELATED APPLICATIONS

This Application claims priority of Taiwan Patent Application No. 111130177, filed on Aug. 11, 2022, the entirety of which is incorporated by reference herein.

BACKGROUND OF THE INVENTION

Field of the Invention

The present disclosure relates in general to the field of radiation oncology, and it relates particularly to a dose control system.

Description of the Related Art

Currently, radiation oncology systems that are widely known, such as boron neutron capture therapy (BNCT) systems, estimate the dose rate (i.e., dose taken within a unit of time) and the irradiation time without considering the drug concentration in plasma of the patient, or under the presumption that the drug concentration in plasma of the patient is a specific theoretical value. However, since the dose rate may be affected by the drug concentration in plasma of the patient, and since the real drug concentration in plasma of the patient may not be equal to the presumed value, known systems may be prone to underestimate or overestimate dose delivered to the patient due to incorrect estimation of the dose rate.

In view of the issues described above, there is a need for a dose control system that calculates the dose rate and the irradiation time in order to control the irradiation device to irradiate the patient for the appropriate amount of time.

BRIEF SUMMARY OF THE INVENTION

A dose control system is provided by the present disclosure. The dose control system includes a processing device configured to execute the steps of (i) obtaining the real drug concentration in plasma of a patient; (ii) calculating a corrected dose rate distribution datum based on the real drug concentration in plasma and a set of correction coefficients; (iii) calculating irradiation time based on the corrected dose rate distribution datum and the prescribed dose distribution datum; and (iv) controlling an irradiation device to irradiate the patient for the irradiation time. The set of correction coefficients is generated based on multiple reference drug concentrations in plasma and multiple reference dose rate distribution data corresponding to the reference drug concentrations in plasma.

In an embodiment, the set of correction coefficients includes one of the reference drug concentrations in plasma, one of the reference dose rate distribution data, and the dose rate change with drug concentration in plasma distribution datum.

In an embodiment, the calculation of the corrected dose rate distribution datum uses Formula <I> as follows:

$$\text{Dose\_rate}(\text{Drug}_{real}, r) = \text{Dose\_rate}(\text{Drug}_{ref}, r) + \frac{\partial \text{Dose\_rate}(\text{Drug}, r)}{\partial \text{Drug}}(\text{Drug}_{real} - \text{Drug}_{ref}) \qquad \langle \text{I} \rangle$$

In Formula <I>, the corrected dose rate distribution datum is represented by Dose_rate($\text{Drug}_{real}$, r), the real drug concentration in plasma is represented by $\text{Drug}_{real}$, a spatial location is represented by r, the reference dose rate distribution datum is represented by Dose_rate($\text{Drug}_{ref}$, r), the reference drug concentrations in plasma is represented by $\text{Drug}_{ref}$, and the dose rate change with drug concentration in plasma distribution datum is represented by $$\frac{\partial \text{Dose\_rate}(\text{Drug}, r)}{\partial \text{Drug}}.$$

In an embodiment, the processing device is further configured to obtain the real beam intensity of the irradiation device. The set of correction coefficients further includes a reference beam intensity corresponding to the reference drug concentration in plasma and the reference dose rate distribution datum.

In an embodiment, the calculation of the corrected dose rate distribution datum uses Formula <II> as follows:

$$\text{Dose\_rate}(\text{Beam}_{real}, \text{Drug}_{real}, r) = \frac{\text{Beam}_{real}}{\text{Beam}_{ref}}\left[\text{Dose\_rate}(\text{Beam}_{ref}, \text{Drug}_{ref}, r) + \frac{\partial \text{Dose\_rate}(\text{Beam}_{ref}, \text{Drug}, r)}{\partial \text{Drug}}(\text{Drug}_{real} - \text{Drug}_{ref})\right] \qquad \langle \text{II} \rangle$$

In Formula <II>, the corrected dose rate distribution datum is represented by Dose_rate($\text{Beam}_{real}$, $\text{Drug}_{real}$, r), the real beam intensity is represented by $\text{Beam}_{real}$, the real drug concentration in plasma is represented by $\text{Drug}_{ref}$, a spatial location is represented by r, the reference dose rate distribution datum is represented by Dose_rate($\text{Beam}_{ref}$, $\text{Drug}_{ref}$, r), the reference beam intensity is represented by $\text{Beam}_{ref}$, the reference drug concentration in plasma is represented by $\text{Drug}_{ref}$, and the dose rate change with drug concentration in plasma distribution datum is represented by $$\frac{\partial \text{Dose\_rate}(\text{Beam}_{ref}, \text{Drug}, r)}{\partial \text{Drug}}.$$

In an embodiment, the real beam intensity is the neutron flux obtained using a neutron measuring device, or the proton current obtained using a beam measuring device configured by an accelerator.

In an embodiment, the processing device is further configured to create the time-dependent function of drug concentration in plasma based on multiple real drug concentrations in plasma, and to create the time-dependent function of beam intensity based on multiple real beam intensities. The processing device is further configured to calculate the time-dependent function of dose rate distribution based on the time-dependent function of drug concentration in plasma, the time-dependent function of beam intensity, and the set of correction coefficients. The processing device is further configured to calculate the time-dependent function of accumulated dose distribution based on the time-dependent function of dose rate distribution. The processing device is further configured to calculate the remaining irradiation time based on the prescribed dose rate distribution datum, the time-dependent function of accumulated dose distribution, and the time-dependent function of dose rate distribution. The processing device is further configured to control the irradiation device to irradiate the patient for the remaining irradiation time.

In an embodiment, the calculation of the time-dependent function of dose rate distribution uses Formula <III> as follows:

$$\text{Dose\_rate}(\text{Beam}(t), \text{Drug}(t), r) = \frac{\text{Beam}(t)}{\text{Beam}_{ref}}\left[\text{Dose\_rate}(\text{Beam}_{ref}, \text{Drug}_{ref}, r) + \frac{\partial \text{Dose\_rate}(\text{Beam}_{ref}, \text{Drug}, r)}{\partial \text{Drug}}(\text{Drug}(t) - \text{Drug}_{ref})\right] \quad \langle \text{III} \rangle$$

In Formula <III>, the time-dependent function of dose rate distribution is represented by Dose_rate(Beam(t), Drug(t), r), the time-dependent function of beam intensity is represented by Beam(t), the time-dependent function of drug concentration in plasma is represented by Drug(t), a spatial location is represented by r, the reference dose rate distribution datum is represented by Dose_rate($\text{Beam}_{ref}$, $\text{Drug}_{ref}$, r), the reference beam intensity is represented by $\text{Beam}_{ref}$, the reference drug concentration in plasma is represented by $\text{Drug}_{ref}$, the dose rate change with drug concentration in plasma distribution datum is represented by $$\frac{\partial \text{Dose\_rate}(\text{Beam}_{ref}, \text{Drug}, r)}{\partial \text{Drug}}.$$

Correspondingly, the calculation of the time-dependent function of accumulated dose distribution uses Formula <IV> as follows:

$$\text{Dose}(t,r) = \int \text{Dose\_rate}(\text{Beam}(t), \text{Drug}(t), r)\,dt \quad \langle \text{IV} \rangle$$

In Formula <IV>, the time-dependent function of accumulated dose distribution is represented by Dose(t, r), and the time-dependent function of dose rate distribution is represented by Dose_rate(Beam(t), Drug(t), r).

The dose control system provided by the present disclosure calculates the dose rate and the irradiation time so as to control the irradiation device to irradiate the patient for an appropriate amount of time. Accordingly, underestimating or overestimating delivered dose to the patient due to incorrect estimation of the dose rate can be avoided.

BRIEF DESCRIPTION OF THE DRAWINGS

The present disclosure can be better understood by reading the subsequent detailed description and examples with references made to the accompanying drawings. Additionally, it should be appreciated that in the flow diagram of the present disclosure, the order of execution for each block can be changed, and/or some of the blocks can be changed, eliminated, or combined.

DETAILED DESCRIPTION OF THE INVENTION

The following description provides embodiments of the invention, which are intended to describe the basic spirit of the invention, but is not intended to limit the invention. For the actual inventive content, reference must be made to the scope of the claims.

In each of the following embodiments, the same reference numbers represent identical or similar elements or components.

Ordinal terms used in the claims, such as "first," "second," "third," etc., are only for convenience of explanation, and do not imply any precedence relation between one another.

Figure 1:
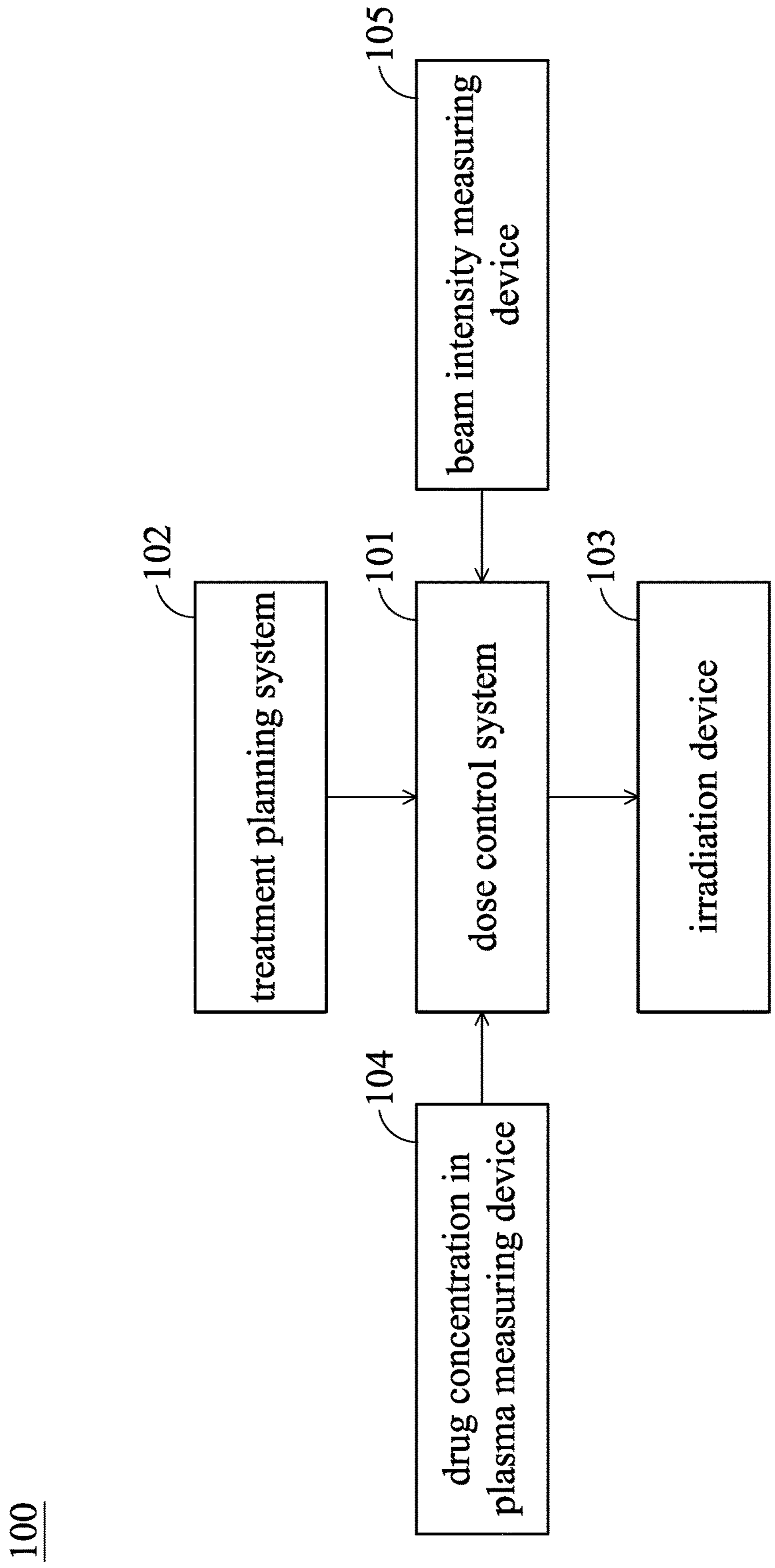
FIG. 1 is a schematic diagram illustrating the application scenario of the processing device of the dose control system, according to an embodiment of the present disclosure.

FIG. 1 is a schematic diagram illustrating the application scenario 100 of a dose control system 101, according to an embodiment of the present disclosure. As shown in FIG. 1, in the application scenario 100, the dose control system 101 may receive data provided by the treatment planning system 102, the drug concentration in plasma measuring device 104, and the beam intensity measuring device 105, and calculate the irradiation time, in order to control the irradiation device 103 to irradiate the patient for the irradiation time. The dose control system 101 may pass through wired or wireless connection to each of the treatment planning system 102, the drug concentration in plasma measuring device 104, and the beam intensity measuring device 105, to receive data provided by each of the treatment planning system 102, the drug concentration in plasma measuring device 104, and the beam intensity measuring device 105. Alternatively, the data provided by the treatment planning system 102, the drug concentration in plasma measuring device 104, and the beam intensity measuring device 105 may be manually input to the dose control system by human. The dose control system 101 may pass through wired or wireless connection to the irradiation device 103, and control the irradiation device 103 to irradiate for the time required through commands or instructions. Alternatively, the irradiation time calculated by the dose control system 101 may be displayed on a displaying device (e.g., LCD display, LED display, OLED display, or plasma display), allowing a human to manipulate the irradiation device 103 manually, so as to control the irradiation device 103 to irradiate the patient for the irradiation time.

The dose control system may be a computer system, such as a personal computer (e.g., laptop computer or notebook computer) or a server computer running an operating system (e.g., Windows, Mac OS, Linux, UNIX . . . , etc.). The dose control system 101 includes a processing device. The processing device may be any device used for executing instructions, such as a central processing unit (CPU), a microprocessor, a controller, a microcontroller, or a state machine. The dose control system 101 may further include a storage device. The storage device may be a storage device including electrically-erasable programmable read-only memory (EEPROM), flash memory, or non-volatile random access memory (NVRAM), such as hard disk drives (HDD), solid state drives (SSD), or optical disks.

The treatment planning system 102 may be a computer system, such as a personal computer (e.g., laptop computer or notebook computer) or a server computer running an operating system (e.g., Windows, Mac OS, Linux, UNIX . . . , etc.). The treatment planning system 102 includes a processing device. The processing device may be any device used for executing instructions, such as a central processing unit (CPU), a microprocessor, a controller, a microcontroller, or a state machine.

Although the dose control system 101 and the treatment planning system 102 are drawn as different systems, the present disclosure is not limited thereto. In some embodiments of the present disclosure, the dose control system and the treatment planning system 102 may be different modules or units of the same computer system.

In an embodiment of the present disclosure, the treatment planning system 102 is used for providing the three-dimensional (3D) dose rate distribution data (i.e., dose rates of each point in the 3D space) corresponding to multiple drug concentrations in plasma, such as the dose rate distribution data when the drug concentration in plasma is 20 ppm, 25 ppm, 30 ppm . . . , etc. These dose rate distribution data may be measured through clinical experiments, or may be calculated using specific algorithms. In an embodiment, the dose rate distribution data are calculated based on organ tissue distribution data, drug absorptance distribution data, material composition parameter data, volume homogenization size, particle tally size, beam parameters, and drug concentration in plasma, with the use of volume homogenization algorithm and Monte Carlo particle transport algorithm. In some embodiments, the treatment planning system 102 further converts the dose rate distribution data into a set of correction coefficients, allowing the dose control system 101 to calculate the corrected dose rate distribution and the irradiation time. In other embodiments, the treatment planning system 102 provides the dose rate distribution data corresponding to multiple drug concentrations in plasma to the dose control system 101, so that the dose control system 101 converts the dose rate distribution data into the set of correction coefficients, allowing to calculate the corrected dose rate distribution and irradiation time subsequently.

The irradiation device 103 may be any neutron emitter for emitting neutrons to the tumor of the patient. The neutrons emitted will be absorbed by the drug (e.g., Boron-10) accumulated in the tumor of the patient, and then the particles with high energy (e.g., lithium-7 or α particles) will be generated to damage the cancer cells locally.

The drug concentration in plasma measuring device 104 may be an inductively coupled plasma mass spectrometry (ICP-MS), an inductively coupled plasma atomic emission spectroscopy (ICP-AES), or any device that may be used for measuring the concentration of drug (e.g., Boron-10) in plasma of the patient.

The beam intensity measuring device 105 may be a neutron measuring device or a beam measuring device configured by an accelerator. The beam intensity measuring device 105 is used for measuring the beam intensity of the irradiation device 103. If the beam intensity measuring device 105 is a neutron measuring device, the measured beam intensity will be neutron flux. If the beam intensity measuring device 105 is a beam measuring device configured by an accelerator, the measured beam intensity will be proton current. In an embodiment, the neutron measuring device and the beam measuring device configured by an accelerator can be a backup beam intensity measuring device 105 for one another, so as to avoid underestimating or overestimating delivered dose caused by the incorrect measurement of one of them.

Figure 2:
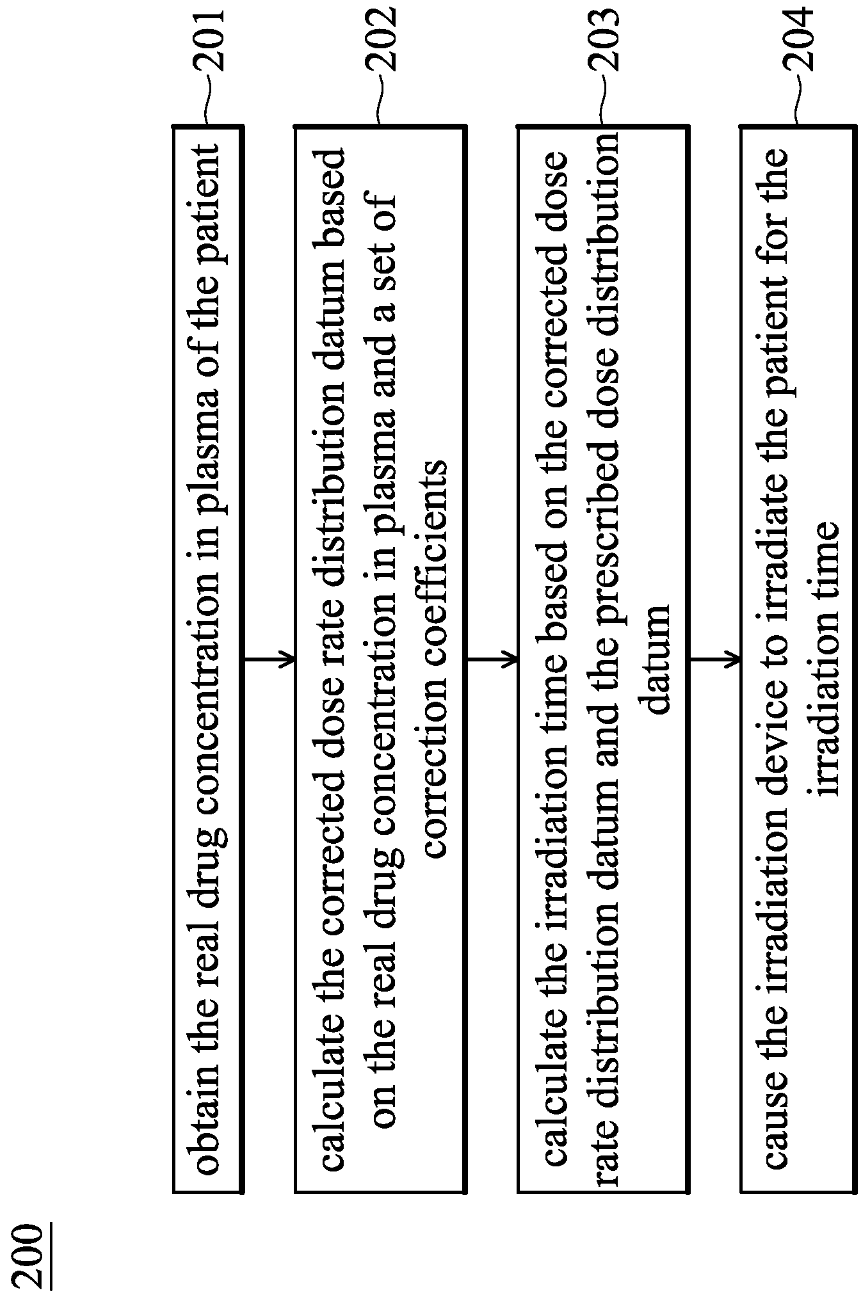
FIG. 2 is a flow diagram illustrating the dose control method executed by the processing device of the dose control system, according to an embodiment of the present disclosure.

FIG. 2 is a flow diagram illustrating a dose control method 200 executed by the processing device of the dose control system 101 in FIG. 1, according to an embodiment of the present disclosure. As shown in FIG. 2, method 200 includes steps 201-204.

Method 200 starts from step 201. In step 201, the real drug concentration in plasma of the patient is obtained. Then, method 200 proceeds to step 202.

In step 202, the corrected dose rate distribution datum is calculated based on the real drug concentration in plasma and a set of correction coefficients. Then, method 200 proceeds to step 203.

In step 203, the irradiation time is calculated based on the corrected dose rate distribution datum and the prescribed dose distribution datum. Then, method 200 proceeds to step 204.

In step 204, the irradiation device is controlled to irradiate the patient for the irradiation time.

In embodiments of the present disclosure, the real drug concentration in plasma can actually be measured using the measuring device (e.g., the drug concentration measuring device 104 in FIG. 1) at the moment just before the patient taking the radiation treatment, or at any time point during the whole process of irradiation.

In an embodiment of the present disclosure, since typically the real drug concentration in plasma of the patient may not be completely equal to the multiple drug concentrations in plasma provided by the treatment planning system 102, the drug concentrations in plasma and the corresponding multiple dose rate distribution data provided by the treatment planning system 102 are only for reference. Therefore, the dose rate distribution datum corresponding to the real drug concentration in plasma of the patient is calculated based on the set of correction coefficients, instead of directly applying one of the dose rate distribution data provided by the treatment planning system 102. The set of correction coefficients is generated based on multiple reference drug concentrations in plasma and the corresponding multiple reference dose rate distribution data provided by the treatment planning system 102. In some embodiments, the set of correction coefficients are converted from multiple reference drug concentrations in plasma and the corresponding multiple reference dose rate distribution data by the treatment planning system 102.

In an embodiment, the set of correction coefficients may include one of the reference drug concentrations in plasma and the corresponding reference dose rate distribution datum, and the dose rate change with drug concentration in plasma distribution (i.e., the dose rate change corresponding to each unit of change of drug concentration in plasma at each point in the 3D space) datum.

Accordingly, the calculation of the corrected dose rate distribution datum may use Formula <I> as follows:

$$\text{Dose\_rate}(\text{Drug}_{real}, r) = \text{Dose\_rate}(\text{Drug}_{ref}, r) + \frac{\partial \text{Dose\_rate}(\text{Drug}, r)}{\partial \text{Drug}}(\text{Drug}_{real} - \text{Drug}_{ref}) \quad \langle I \rangle$$

In Formula <I>, the corrected dose rate distribution datum is represented by Dose_rate($\text{Drug}_{real}$, r), the real drug concentration in plasma is represented by $\text{Drug}_{real}$, a spatial location is represented by r (r may represent a coordinate in the 3D spatial coordinate system), the reference dose rate distribution datum is represented by Dose_rate($Drug_{ref}$, r), the reference drug concentrations in plasma is represented by $Drug_{ref}$, and the dose rate change with drug concentration in plasma distribution datum is represented by $$\frac{\partial \text{Dose\_rate}(\text{Drug}, r)}{\partial \text{Drug}}.$$

Corresponding to Formula <I>, the calculation of irradiation time in step 204 may use Formula <V> as follows:

$$T_f = \min\left(\frac{\text{Prescription\_dose}(r)}{\text{Dose\_rate}(\text{Drug}_{real}, r)}\right) \quad \langle V \rangle$$

In formula <V>, the irradiation time is represented by $T_f$, the corrected dose rate distribution datum calculated using Formula <I> is represented by Dose_rate($Drug_{real}$, r), the prescribed dose distribution (i.e., the prescribed dose at each points in the 3D space) datum is represented by Prescription_dose(r), and min( ) represents the minimal one of $$\frac{\text{Prescription\_dose}}{\text{Dose\_rate}(Drug_{real}, r)}$$

corresponding to all the r values (i.e., all locations). As such, overdosing may be avoided for any location of the patient.

In another embodiment, in view of that the dose rate may also be affected by the beam intensity, the set of correction coefficients may further include a reference beam intensity corresponding to the reference drug concentration in plasma and the reference dose rate distribution datum, besides one of reference drug concentrations in plasma, the reference dose rate distribution datum corresponding to the one of reference drug concentrations in plasma, and the dose rate change with drug concentration in plasma distribution datum that are previously described.

Accordingly, the calculation of the corrected dose rate distribution datum may use Formula <II> as follows:

$$\text{Dose\_rate}(Beam_{real}, Drug_{real}, r) = \frac{Beam_{real}}{Beam_{ref}}\left[\text{Dose\_rate}(Beam_{ref}, Drug_{ref}, r) + \frac{\partial \text{Dose\_rate}(Beam_{ref}, \text{Drug}, r)}{\partial \text{Drug}}(Drug_{real} - Drug_{ref})\right]. \quad \langle II \rangle$$

In Formula <II>, the corrected dose rate distribution datum is represented by Dose_rate($Beam_{real}$, $Drug_{real}$, r), the real beam intensity is represented by $Beam_{real}$, the real drug concentration in plasma is represented by $Drug_{ref}$, a spatial location is represented by r, the reference dose rate distribution datum is represented by Dose_rate($Beam_{ref}$, $Drug_{ref}$, r), the reference beam intensity is represented by $Beam_{ref}$, the reference drug concentration in plasma is represented by $Drug_{ref}$, and the dose rate change with drug concentration in plasma distribution datum is represented by $$\frac{\partial \text{Dose\_rate}(Beam_{ref}, \text{Drug}, r)}{\partial \text{Drug}}.$$

Corresponding to Formula <II>, the calculation of the irradiation time in step 204 may use Formula <VI> as follows:

$$T_f = \min\left(\frac{\text{Prescription\_dose}(r)}{\text{Dose\_rate}(Beam_{real}, Drug_{real}, r)}\right). \quad \langle VI \rangle$$

In Formula <VI>, the irradiation time is represented by $T_f$, the corrected dose rate distribution datum calculated using Formula <II> is represented by Dose_rate($Beam_{real}$, $Drug_{real}$, r), the prescribed dose distribution (i.e., the prescribed dose at each points in the 3D space) datum is represented by Prescription_dose(r), and min( ) represents the minimal one of $$\frac{\text{Prescription\_dose}(r)}{\text{Dose\_rate}(Beam_{real}, Drug_{real}, r)}$$

corresponding to all the r values (i.e., all locations). As such, overdosing may be avoided for any location of the patient.

In some embodiments, it is considered that the drug concentration in plasma of the patient typically decreases or increases with time gradually during the irradiation, such that the drug concentration in plasma that is measured at the beginning (e.g., at the moment just before the patient taking the radiation treatment) may not be equal to the real drug concentration in plasma during the irradiation, and the dose rate will not be constant anymore. Therefore, there is a need to consider the real drug concentration in plasma change with time, and to calculate the time-dependent function of dose rate distribution (i.e., the correspondence between time and dose rate distribution), in order to estimate the remaining irradiation time more accurately and immediately.

Figure 3:
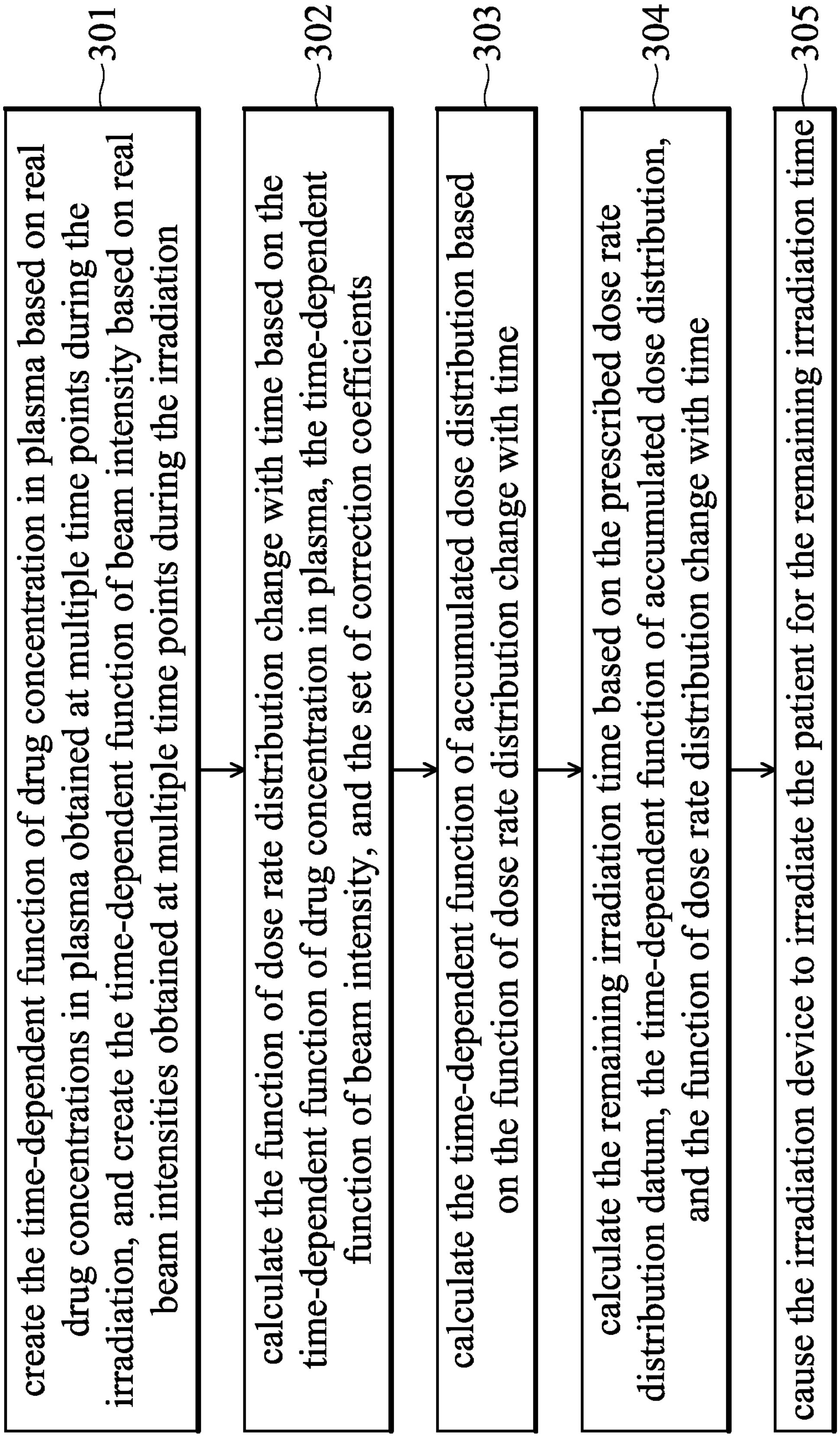
FIG. 3 is a flow diagram illustrating the dose control method executed by the processing device of the dose control system with the consideration of how the parameters change with time, according to an embodiment of the present disclosure.

FIG. 3 is a flow diagram illustrating a dose control method 300 executed by the processing device of the dose control system in FIG. 1. As shown in FIG. 3, method 300 includes steps 301-305.

Method 300 starts from step 301. In step 301, the time-dependent function of drug concentration in plasma (i.e., the correspondence between time and drug concentration in plasma) is created based on real drug concentrations in plasma obtained at multiple time points during the irradiation, and the time-dependent function of beam intensity (i.e., the correspondence between time and beam intensity) is created based on real beam intensities obtained at multiple time points during the irradiation. Then, method 300 proceeds to step 302.

In step 302, the time-dependent function of dose rate distribution (i.e., the correspondence between time and dose rate distribution) is calculated based on the time-dependent function of drug concentration in plasma, the time-dependent function of beam intensity, and the set of correction coefficients. Then, method 300 proceeds to step 303.

In step 303, the time-dependent function of accumulated dose distribution (i.e., the correspondence between time and the accumulated doses at each point in the 3D space) is calculated based on the time-dependent function of dose rate distribution. Then, method 300 proceeds to step 304.

In step 304, the remaining irradiation time is calculated based on the prescribed dose rate distribution datum, the time-dependent function of accumulated dose distribution, and the time-dependent function of dose rate distribution. Then, method 300 proceeds to step 305.

In step 305, the irradiation device is controlled to irradiate the patient for the remaining irradiation time.

In an embodiment, the calculation of the time-dependent function of dose rate distribution may use Formula <III> as follows:

$$\text{Dose\_rate}(\text{Beam}(t), \text{Drug}(t), r) = \frac{\text{Beam}(t)}{Beam_{ref}}\left[\text{Dose\_rate}(Beam_{ref}, Drug_{ref}, r) + \frac{\partial \text{Dose\_rate}(Beam_{ref}, \text{Drug}, r)}{\partial \text{Drug}}(\text{Drug}(t) - Drug_{ref})\right] \quad \langle \text{III} \rangle$$

In Formula <III>, the time-dependent function of dose rate distribution is represented by Dose_rate(Beam(t), Drug(t), r), the time-dependent function of beam intensity is represented by Beam(t), the time-dependent function of drug concentration in plasma is represented by Drug(t), a spatial location is represented by r, the reference dose rate distribution datum is represented by Dose_rate($Beam_{ref}$, $Drug_{ref}$, r), the reference beam intensity is represented by $Beam_{ref}$, the reference drug concentration in plasma is represented by $Drug_{ref}$, the dose rate change with drug concentration in plasma distribution datum is represented by $$\frac{\partial \text{Dose\_rate}(Beam_{ref}, \text{Drug}, r)}{\partial \text{Drug}},$$

and t may represent any time point during the irradiation (e.g., the $t^{th}$ second from the beginning of irradiation).

Corresponding to Formula <III>, the calculation of the time-dependent function of accumulated dose distribution may use Formula <IV> as follows:

$$\text{Dose}(t,r) = \int \text{Dose\_rate}(\text{Beam}(t), \text{Drug}(t), r)\,dt \quad \langle \text{IV} \rangle$$

In Formula <IV>, the time-dependent function of accumulated dose distribution is represented by Dose(t, r), and the time-dependent function of dose rate distribution calculated by Formula <III> is represented by Dose_rate(Beam(t), Drug(t), r).

Corresponding to Formula <III> and Formula <IV>, the calculation of the remaining irradiation time may use Formula <VII> as follows:

$$T_{remain} = \min\left(\frac{\text{Prescription\_dose}(r) - \text{Dose}(t, r)}{\text{Dose\_rate}(\text{Beam}(t), \text{Drug}(t) r)}\right) \quad \langle \text{VII} \rangle$$

In Formula <VII>, the remaining irradiation time is represented by $T_{remain}$, the time-dependent function of dose rate distribution calculated by Formula <III> is represented by Dose_rate(Beam(t), Drug(t), r), the prescribed dose distribution (i.e., the prescribed dose at each points in the 3D space) is represented by Prescription_dose(r), and min( ) represents the minimal one of $$\frac{\text{Prescription\_dose}(r) - \text{Dose}(t, r)}{\text{Dose\_rate}(\text{Beam}(t), \text{Drug}(t) r)}$$

corresponding to all the r values (i.e., all locations). As such, overdosing may be avoided for any location of the patient.

In further embodiments, the expected total dose Dose(r) for the whole course of treatment may be calculated based on the time-dependent function of accumulated dose distribution and the remaining irradiation time $T_{remain}$. Specifically, by adding the current time point and $T_{remain}$, the expected total irradiation time $T_{total}$ for the whole course of treatment may be obtained (e.g., if currently the patient has been irradiated for 20 minutes, and the remaining irradiation time is 10 minutes, then the total irradiation time will be 20+10=30 minutes). Afterwards, $T_{total}$ is substituted into Formula <IV>, in other words $\int_0^{T_{total}}$ Dose_rate(Beam(t), Drug(t), r) dt is calculated, and the expected total dose Dose(r) for the whole course of treatment may be obtained.

The methods described above can be carried out using computer-executable instructions. For example, these instructions may include instructions and data that allow a general-purpose computer, a special-purpose computer, or a special-purpose processing device to execute specific functions or a set of functions. Some of the computer resources may be accessed through a network.

The dose control system provided by the present disclosure calculates the dose rate and the irradiation time so as to control the irradiation device to irradiate the patient for an appropriate amount of time. Accordingly, underestimating or overestimating delivered dose to the patient due to incorrect estimation of the dose rate can be avoided.

The above paragraphs are described with multiple aspects. Obviously, the teachings of the specification may be performed in multiple ways. Any specific structure or function disclosed in the examples is only a representative situation. According to the teachings of the specification, it should be noted by those skilled in the art that any aspect disclosed may be performed individually, or that more than two aspects could be combined and performed.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A dose control system, comprising a processing device configured to execute the following steps:

obtaining a real drug concentration in plasma of a patient;

calculating a corrected dose rate distribution datum based on the real drug concentration in plasma and a set of correction coefficients;

calculating irradiation time based on the corrected dose rate distribution datum and a prescribed dose distribution datum; and controlling an irradiation device to irradiate the patient for the irradiation time;

wherein the set of correction coefficients is generated based on multiple reference drug concentrations in plasma and multiple reference dose rate distribution data corresponding to the reference drug concentrations in plasma.

2. The dose control system as claimed in claim 1, wherein the set of correction coefficients comprises one of the reference drug concentrations in plasma, one of the reference dose rate distribution data, and a dose rate change with drug concentration in plasma distribution datum.

3. The dose control system as claimed in claim 2, wherein the calculation of the corrected dose rate distribution datum uses the following formula:

$$\text{Dose\_rate}(Drug_{real}, r) = \text{Dose\_rate}(Drug_{ref}, r) + \frac{\partial \text{Dose\_rate}(\text{Drug}, r)}{\partial \text{Drug}}(Drug_{real} - Drug_{ref})$$

wherein the corrected dose rate distribution datum is represented by Dose_rate($Drug_{real}$, r), the real drug concentration in plasma is represented by $Drug_{real}$, a spatial location is represented by r, the reference dose rate distribution datum is represented by Dose_rate ($Drug_{ref}$, r), the reference drug concentrations in plasma is represented by $Drug_{ref}$, and the dose rate change with drug concentration in plasma distribution datum is represented by $$\frac{\partial \text{Dose\_rate}(\text{Drug}, r)}{\partial \text{Drug}}.$$

4. The dose control system as claimed in claim 2, wherein the processing device is further configured to obtain a real beam intensity of the irradiation device;

wherein the set of correction coefficients further comprises a reference beam intensity corresponding to the reference drug concentration in plasma and the reference dose rate distribution datum.

5. The dose control system as claimed in claim 4, wherein the calculation of the corrected dose rate distribution datum uses the following formula:

$$\text{Dose\_rate}(Beam_{real}, Drug_{real}, r) = \frac{Beam_{real}}{Beam_{ref}}\left[\text{Dose\_rate}(Beam_{ref}, Drug_{ref}, r) + \frac{\partial \text{Dose\_rate}(Beam_{ref}, \text{Drug}, r)}{\partial \text{Drug}}(Drug_{real} - Drug_{ref})\right]$$

wherein the corrected dose rate distribution datum is represented by Dose_rate($Beam_{real}$, $Drug_{real}$, r), the real beam intensity is represented by $Beam_{real}$, the real drug concentration in plasma is represented by $Drug_{ref}$, a spatial location is represented by r, the reference dose rate distribution datum is represented by Dose_rate ($Beam_{ref}$, $Drug_{ref}$, r), the reference beam intensity is represented by $Beam_{ref}$, the reference drug concentration in plasma is represented by $Drug_{ref}$, and the dose rate change with drug concentration in plasma distribution datum is represented by $$\frac{\partial \text{Dose\_rate}(Beam_{ref}, \text{Drug}, r)}{\partial \text{Drug}}.$$

6. The dose control system as claimed in claim 4, wherein the real beam intensity is a neutron flux obtained using a neutron measuring device, or a proton current obtained using a beam measuring device configured by an accelerator.

7. The dose control system as claimed in claim 2, wherein the processing device is further configured to execute the following steps:

creating a time-dependent function of drug concentration in plasma based on multiple real drug concentrations in plasma, and creating a time-dependent function of beam intensity based on multiple real beam intensities, wherein the real drug concentrations in plasma and the real beam intensities are obtained at multiple time points during irradiation;

calculating a time-dependent function of dose rate distribution based on the time-dependent function of drug concentration in plasma, the time-dependent function of beam intensity, and the set of correction coefficients;

calculating a time-dependent function of accumulated dose distribution based on the time-dependent function of dose rate distribution;

calculating remaining irradiation time based on the prescribed dose rate distribution datum, the time-dependent function of accumulated dose distribution, and the time-dependent function of dose rate distribution; and controlling the irradiation device to irradiate the patient for the remaining irradiation time.

8. The dose control system as claimed in claim 7, wherein the calculation of the time-dependent function of dose rate distribution uses the following formula:

$$\text{Dose\_rate}(\text{Beam}(t), \text{Drug}(t), r) = \frac{\text{Beam}(t)}{Beam_{ref}}\left[\text{Dose\_rate}(Beam_{ref}, Drug_{ref}, r) + \frac{\partial \text{Dose\_rate}(Beam_{ref}, \text{Drug}, r)}{\partial \text{Drug}}(\text{Drug}(t) - Drug_{ref})\right]$$

wherein the time-dependent function of dose rate distribution is represented by Dose_rate(Beam(t), Drug(t), r), the time-dependent function of beam intensity is represented by Beam(t), the time-dependent function of drug concentration in plasma is represented by Drug(t), a spatial location is represented by r, the reference dose rate distribution datum is represented by Dose_rate ($Beam_{ref}$, $Drug_{ref}$, r), the reference beam intensity is represented by $Beam_{ref}$, the reference drug concentration in plasma is represented by $Drug_{ref}$, the dose rate change with drug concentration in plasma distribution datum is represented by $$\frac{\partial \text{Dose\_rate}(Beam_{ref}, \text{Drug}, r)}{\partial \text{Drug}};$$

and wherein the calculation of the time-dependent function of accumulated dose distribution uses the following formula:

$$\text{Dose}(t,r)=\int \text{Dose\_rate}(\text{Beam}(t),\text{Drug}(t),r)dt$$

wherein the time-dependent function of accumulated dose distribution is represented by Dose(t, r), and the time-dependent function of dose rate distribution is represented by Dose_rate(Beam(t), Drug(t), r).

* * * * *